United States Patent
Tovey (10) Patent No.: US 8,922,860 B2
(45) Date of Patent: Dec. 30, 2014

(54) MOTION CONTROL SYSTEMS AND METHODS FOR BIOSENSOR SCANNING

(75) Inventor: Cameron John Tovey, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 364 days.

(21) Appl. No.: 13/613,141

(22) Filed: Sep. 13, 2012

(65) Prior Publication Data

US 2013/0063724 A1 Mar. 14, 2013

Related U.S. Application Data

(60) Provisional application No. 61/534,604, filed on Sep. 14, 2011.

(51) Int. Cl.
| | | |
|---|---|---|
| *G02B 26/08* | (2006.01) | |
| *G01N 21/25* | (2006.01) | |
| *G01N 21/77* | (2006.01) | |

(52) U.S. Cl.
CPC ............ *G01N 21/253* (2013.01); *G01N 21/774* (2013.01); *G01N 2201/10* (2013.01); *G01N 2201/105* (2013.01); *G01N 2021/7773* (2013.01); *G01N 2021/7793* (2013.01); *G01N 2021/7796* (2013.01); *G01N 2201/1042* (2013.01)
USPC ...................................................... 359/199.1

(58) Field of Classification Search
CPC . G02B 26/105; G02B 26/101; G02B 26/0833
See application file for complete search history.

(56) References Cited

U.S. PATENT DOCUMENTS

| | | | |
|---|---|---|---|
| 4,815,843 | A | 3/1989 | Tiefenthaler et al. |
| 5,738,825 | A | 4/1998 | Rudigier et al. |
| 7,424,187 | B2 | 9/2008 | Montgomery et al. |
| 7,528,364 | B2 | 5/2009 | Farinas et al. |
| 7,869,910 | B1 | 1/2011 | Bandyopadhyay et al. |
| 2002/0177135 | A1* | 11/2002 | Doung et al. ..................... 435/6 |
| 2006/0141611 | A1 | 6/2006 | Frutos et al. |
| 2006/0205058 | A1 | 9/2006 | Frutos et al. |
| 2007/0098600 | A1* | 5/2007 | Kayyem ...................... 422/102 |
| 2007/0202543 | A1 | 8/2007 | Gollier et al. |
| 2013/0194647 | A1* | 8/2013 | Tovey ....................... 359/197.1 |

FOREIGN PATENT DOCUMENTS

WO 2011/017147 2/2011

* cited by examiner

*Primary Examiner* — Jennifer L. Doak
(74) *Attorney, Agent, or Firm* — John. L. Haack (57) ABSTRACT

Motion control system and method for biosensor scanning that include inputting to a multi-axis motion controller move commands associated with the scan path as defined by multiple axes. The multiple axes including an x-baseline coordinate $x_0$, a y-baseline coordinate $y_0$, an x-direction oscillation amplitude $x_1$, a y-direction oscillation amplitude $y_1$, an oscillation frequency f and a phase $\phi$. The multi-axis motion controller outputs digital commanded positions for each of the multiple axes. A post-processor receives the commanded positions and generates parameterized commanded positions x and y that each include a baseline motion component and an oscillating motion component. The parameterized commanded positions cause the scanning optical system to deflect the light beam to scan the beam spot over the scan path to scan the biosensor.

21 Claims, 10 Drawing Sheets

MOTION CONTROL SYSTEMS AND METHODS FOR BIOSENSOR SCANNING

CROSS-REFERENCE TO RELATED APPLICATIONS

The entire disclosure of any publication or patent document mentioned herein is incorporated by reference.

This application claims the benefit of priority under 35 U.S.C. §119 of U.S. Provisional Application Ser. No. 61/534,604, filed Sep. 14, 2011.

This application is related to U.S. Provisional Application Ser. No. 61/445,266, filed on Feb. 22, 2011, but does not claim priority thereto.

FIELD

The present disclosure relates to biosensor scanning such as performed in label-independent optical reader systems, and in particular to motion control systems and methods for biosensor scanning.

BACKGROUND

Manufacturers of optical reader systems seek to design a new and improved optical reader systems that can be used to interrogate a resonant waveguide grating biosensor to determine if a biomolecular binding event (e.g., binding of a drug to a protein) occurred on a surface of the biosensor. Of present interest are improved scanning systems and methods that reduce vibrations and resonances, and that generally improve the quality and efficiency of the biosensor readings obtained from the biosensor scanning. Such new and improved biosensor scanning systems and methods that have such capability are the subject of the present disclosure.

SUMMARY

An aspect of the disclosure is a method of defining a scan path using a scanning optical system to scan a beam spot formed by a light beam over one or more biosensors supported by a microplate. The method includes inputting to a multi-axis motion controller move commands associated with the scan path as defined by each of the multiple axes, the multiple axes including-baseline coordinate $x_0$, a y-baseline coordinate $y_0$, an x-direction oscillation amplitude $x_1$, a y-direction oscillation amplitude $y_1$, an oscillation frequency f and a phase $\phi$. The method also includes outputting from the multi-axis motion controller commanded positions for each of the six axes. The method further includes receiving the commanded positions with a post-processor and generating therein parameterized commanded positions x and y as defined by the following equations where t is time and OSC is an oscillatory function:

$$x=x_0+x_1 \cdot OSC(2\pi \cdot f \cdot t+\phi) \text{ and } y=y_0+y_1 \cdot OSC(2\pi \cdot f \cdot t+\phi).$$

The method additionally includes inputting the parameterized commanded positions x and y to a scanning optical system to cause the scanning optical system to deflect the light beam to scan the beam spot over the scan path.

Another aspect of the disclosure is a system for defining a scan path for a beam spot formed by a light beam over a microplate that operably supports at least one biosensor. The system includes a multi-axis motion controller configured to receive move commands associated with the scan path as defined by respective axes, the axes including an x-baseline coordinate $x_0$, a y-baseline coordinate $y_0$, an x-direction oscillation amplitude $x_1$, a y-direction oscillation amplitude $y_1$, an oscillation frequency f and a phase $\phi$, and to output commanded positions for each of the multiple axes. The system also includes a post-processor configured to receive the commanded positions x and y and generate therefrom parameterized commanded positions x and y defined by the following equations where t is time and OSC is an oscillatory function:

$$x=x_0+x_1 \cdot OSC(2\pi \cdot f \cdot t+\phi) \text{ and } y=y_0+y_1 \cdot OSC(2\pi \cdot f \cdot t+\phi).$$

The system also includes a scanning optical system configured to receive the parameterized commanded positions and in response thereto deflect the light beam to scan the beam spot over the scan path.

Another aspect of the disclosure is a method of defining a scan path for a beam spot formed by a scanning optical system. The method includes inputting to a multi-axis motion controller move commands associated with the scan path as defined by multiple axes, the multiple axes including an x-baseline coordinate $x_0$, y-a baseline coordinate $y_0$, an x-direction oscillation amplitude $x_1$, a y-direction oscillation amplitude $y_1$, an oscillation frequency f and a phase $\phi$. The method also includes outputting from the multi-axis motion controller digital commanded positions x and y for each of the multiple axes. The method further includes receiving the digital commanded positions x and y with a post-processor and generating therein analog or pulse-width-modulated (PWM) parameterized commanded positions x and y that each include a baseline motion component and an oscillating motion component. The method additionally includes inputting the analog or PWM parameterized commanded positions x and y to a scanning optical system to cause the scanning optical system to deflect a light beam to scan the beam spot over the scan path. In an example of the method, the analog parameterized commanded positions x and y are defined by the following equations where t is time:

$$x=x_0+x_1 \cdot \sin(2\pi \cdot f \cdot t+\phi) \text{ and } y=y_0+y_1 \cdot \sin(2\pi \cdot f \cdot t+\phi).$$

These and other advantages of the disclosure will be further understood and appreciated by those skilled in the art by reference to the following written specification, claims and appended drawings.

BRIEF DESCRIPTION OF THE DRAWINGS

A more complete understanding of the present disclosure may be had by reference to the following detailed description when taken in conjunction with the accompanying drawings, wherein.

DETAILED DESCRIPTION

Reference is now made to embodiments of the disclosure, exemplary embodiments of which are illustrated in the accompanying drawings. The claims are incorporated into and constitute part of the Detailed Description.

In the discussion below, in certain descriptions, the angle $\theta$ is a "deflection angle" and refers to the angle of incident optical beams 134I relative to optical axis A1 as these optical beams leave scanning mirror device 260. Also in certain descriptions, the angle $\beta$ refers to an "incidence angle" that the incident optical beams 134I make relative to the surface normal N of microplate 170. Microplate 170 is assumed to lie in an X-Y plane thereby defining deflection angles $\theta_X$ and $\theta_Y$ and incident angles $\beta_X$ and $\beta_Y$ associated with incident optical beam(s) 134I. In certain descriptions, the angle $\theta$ is used in place of angle $\beta$ as described above, and one skilled in the art will understand from the context of the discussion the meaning of the particular symbol used for a given angle. Likewise, in certain other descriptions, the angle $\theta$ is used as a polar angle in connection with defining parameterized commanded positions in polar coordinates for a scan path of a light spot over the biosensor(s), as discussed below.

Optical Reader System

Figure 1:
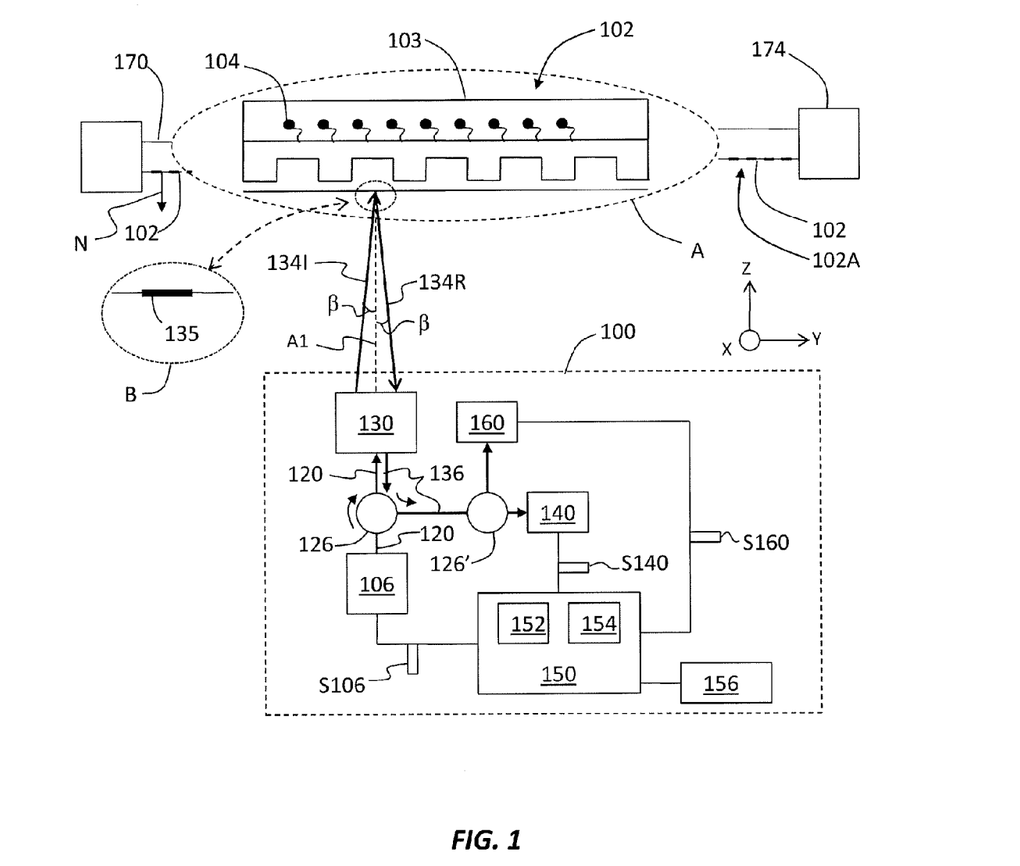
FIG. 1 is a generalized schematic diagram of an optical reader system of the disclosure.

FIG. 1 is a generalized schematic diagram of an optical reader system ("system") 100 of the present disclosure and used to interrogate one or more biosensors 102 each having a surface 103 to determine if a biological substance 104 is present on the biosensor. Inset A shows a close-up of an exemplary biosensor 102. Biosensor 102 may be, for example, a resonant waveguide grating (RWG) biosensor, a surface plasmon resonance (SPR) biosensor, or like biosensor. U.S. Pat. No. 4,815,843 describes example biosensors 102.

Figure 2:
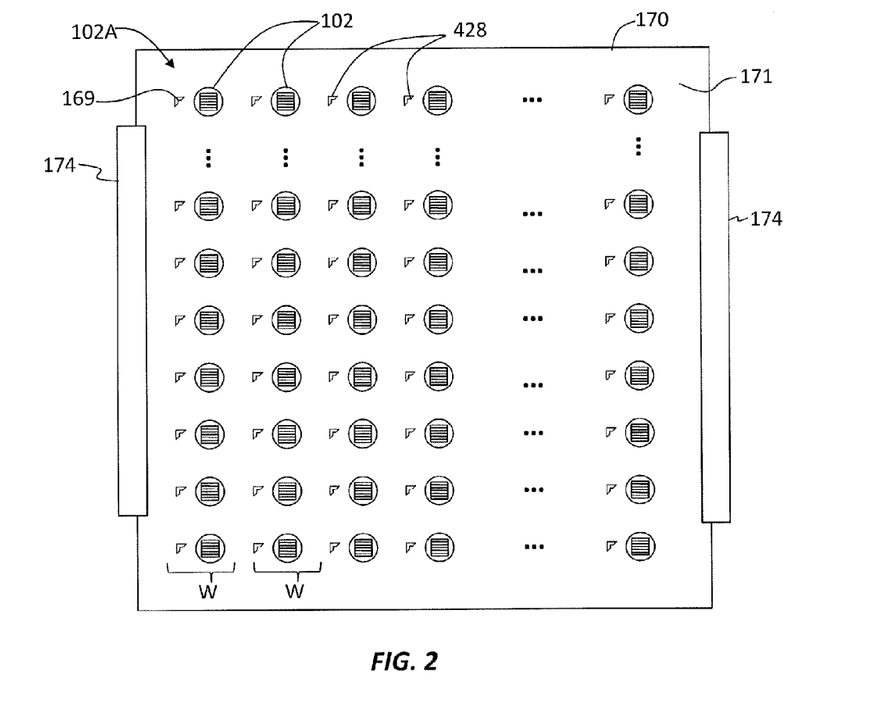
FIG. 2 shows an exemplary biosensor array operably supported in regions or "wells" of a microplate, which in turn is held by a microplate holder.

FIG. 2 shows an exemplary configuration where biosensors 102 are arranged in an array 102A and operably supported in regions or "wells" W of a microplate 170 having a surface 171. An exemplary biosensor array 102A has a 4.5 mm pitch for biosensors 102 that are 2 mm square, and includes 16 biosensors per column and 24 biosensors in each row. In an example, microplate 170 includes fiducials 169 on microplate surface 171 that can be used to position, align, or both the microplate 170 in system 100 relative to a reference location. A microplate holder 174 is also shown holding microplate 170. Many different types of plate holders can be used as microplate holder 174. U.S. Pat. No. 5,738,825 describes example microplates 170.

With reference again to FIG. 1, optical reader system 100 includes a light source assembly 106 (e.g., lamp, laser, diode, filters, attenuators, etc.) that generates light 120. Light 120 is directed by a coupling device 126 (e.g., a circulator, optical switch, fiber splitter or the like) to a scanning optical system 130 that has an associated optical axis A1 and that transforms light 120 into an incident optical beam 134I, which forms a beam spot 135 at biosensor 102 (see inset B). Incident optical beam 134I (and thus beam spot 135) is scanned over the biosensor 102 by the operation of scanning optical system 130. In an example, the biosensor 102 is moved (i.e., by moving microplate 170) so that the incident optical beam can be scanned across the biosensor 102. Also in an example, the incident optical beam 134I is scanned across a stationary biosensor 102 using scanning optical system 130, as described further below. In another example, both scanning and microplate movement can be employed.

Incident optical beam 134I reflects from biosensor 102, thereby forming a reflected optical beam 134R. Reflected optical beam 134R is received by scanning optical system 130 and light 136 therefrom (hereinafter, "guided light signal") is directed by coupling device 126 to a spectrometer unit 140, which generates an electrical signal S140 representative of the spectra of the reflected optical beam. In embodiments, a system controller ("controller") 150 having a processor unit ("processor") 152 and a memory unit ("memory") 154 then receives electrical signal S140 and stores in the memory the raw spectral data, which is a function of a position (and possibly time) on biosensor 102.

Figure 3:
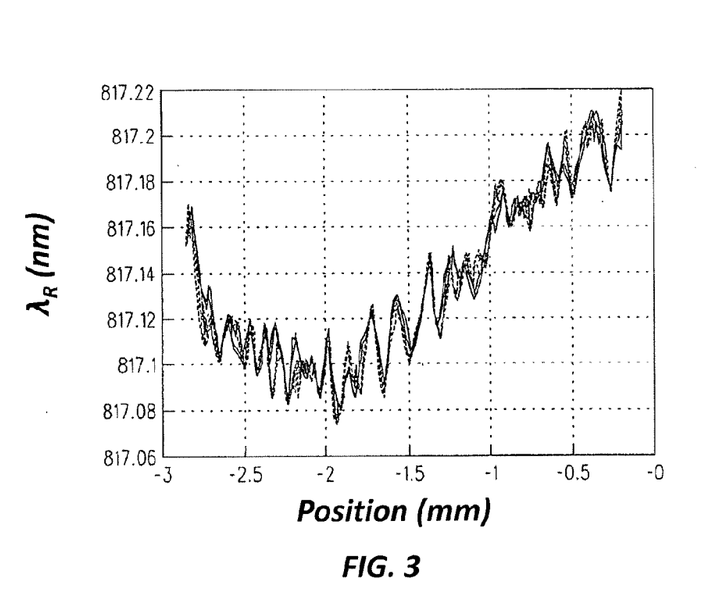
FIG. 3 is a plot of resonant wavelength $\lambda_R$ (nm) vs. position (mm) across the biosensor.

Thereafter, processor 152 analyzes the raw spectral data based on instructions stored therein or in memory 152. The result is a spatial map of resonant wavelength ($\lambda_R$) data such as shown by way of illustration in FIG. 3, which shows the calculated resonance centroid as a function of the position of the scanning spot across the sensor for a number of different scans. The variation of the resonance wavelength indicates if a chemical or biological reaction happened for a specific sensor.

In embodiments, controller 150 includes or is operably connected to a display unit 156 that displays measurement information such as spectra plots, resonant wavelength plots, and other measurement results, as well as system status and performance parameters. In another embodiments, spectra can be processed immediately so that only the wavelength centroid is stored in memory 154.

Also in example, system 10 includes a photodetector 160 used to detect the intensity of reflected optical beam 134R without the reflected optical beam passing to spectrometer 140. This configuration is useful when performing diagnostic measurements or for determining the position of microplate 170 using the positioning methods described in greater detail below. In an example, photodetector 160 is operably connected to a second circulator 126' located between first circulator 126 and spectrometer 140. Photodetector 160 generates a photodetector signal S160 that is provided to controller 150 and is processed using, for example, processor 152 therein. Intensity data from photodetector 160 can also be stored in memory 154.

Biosensors

Example biosensors 102 make use of changes in the refractive index at sensor surface 103 that affect the waveguide coupling properties of incident optical beam 134I and reflected optical beam 134R to enable label-free detection of biological substance 104 (e.g., cell, molecule, protein, drug, chemical compound, nucleic acid, peptide, carbohydrate) on the biosensor. Biological substance 104 may be located within a bulk fluid deposited on biosensor surface 103, and the presence of this biological substance alters the index of refraction at the biosensor surface.

To detect biological substance 104, biosensor 102 can be probed with incident optical beam 134I while reflected optical beam 134R is received at spectrometer unit 140. Controller 150 can be configured (e.g., processor 152 can be programmed) to determine if there are any changes (e.g., 1 part per million) in the biosensor refractive index caused by the presence of biological substance 104. In embodiments, biosensor surface 103 can be coated with, for example, biochemical compounds (not shown) that only allow surface attachment of specific complementary biological substances 104, thereby enabling biosensor 102 to be both highly sensitive and highly specific. In this way, system 100 and biosensor 102 can be used to detect a wide variety of biological substances 104. Likewise, biosensor 102 can be used to detect the movements or changes in cells immobilized to biosensor surface 103, for example, when the cells move relative to the biosensor or when they incorporate or eject material a refractive index change occurs.

If multiple biosensors 102 are operably supported as an array 102A in wells W of microplate 170, which in turn is supported by microplate holder 174, then they can be used to enable high-throughput drug or chemical screening studies. For a more detailed discussion about the detection of a biological substance 104 (or a biomolecular binding event) using scanning optical reader systems, reference is made to U.S. Patent Application Publication No. 2006/0141611. Other optical reader systems are described in U.S. Pat. No. 7,424,187 and U.S. Patent Application Publications No. 2006/0205058 and 2007/0202543.

Spectral Interrogation

The most commonly used technique for measuring biochemical or cell assay events occurring on RWG-based biosensors 102 is spectral interrogation. Spectral interrogation entails illuminating biosensor 102 with a multi-wavelength or broadband beam of light (incident optical beam 134I), collecting the reflected light (reflected optical beam 134R), and analyzing the reflected spectrum with spectrometer unit 140.

Figure 4:
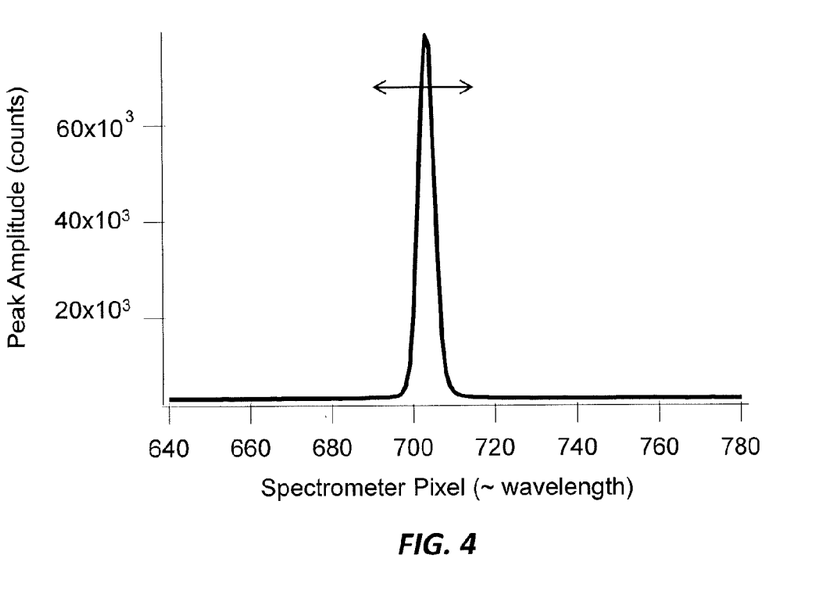
FIG. 4 is a plot of the peak amplitude (photon counts) versus spectrometer pixel location, which corresponds to wavelength.

An exemplary reflection spectrum from an example spectrometer unit 140 is shown in FIG. 4, where the "peak amplitude" is the number of photon counts as determined by an analog-to-digital (A/D) converter in the spectrometer. When chemical binding occurs at biosensor surface 103, the resonance shifts slightly in wavelength as indicated by the double arrow, and this shift can be detected by spectrometer unit 140.

While the general concept of spectral interrogation of biosensor 102 is straightforward, the implementation details of how light can be delivered to and collected from the biosensor can have a major impact on the quality of the data and practical utility of system 100. For example, due to inevitable non-homogeneity of the resonant wavelength $\lambda_R$ across biosensors 102, the measured resonant wavelength $\lambda_R$ is extremely sensitive to the position of incident optical beam 134I over the biosensor.

Further, variation in absolute readings between microplates 170 is large compared with the wavelength shift. There can be significant differences between absolute readings of biosensors 102 on the same microplate, between microplates, and between readings of the same microplate taken by two different optical readers. Optical readers currently need at least two readings to detect activity. The reported measurement is a wavelength shift between the current condition and an earlier "baseline" condition, such as before the addition of biological substance 104, such as cells or proteins. Typically, microplate 170 needs to be removed and repositioned between some measurements to add reagents or so that other microplates 170 can be measured while the reagents take effect. This typically leads to errors in plate position, which in turn causes errors in the reading of biosensors 102.

Biosensors 102 are also inherently non-homogeneous due to manufacturing processes used to make them. For example, there is typically a variation in the absolute resonant wavelength within each biosensor. Consequently, any wavelength shift between readings of a biosensor can only be attributed to biochemical change if the same point(s) on the biosensor are measured. An error of 0.01 mm in the position of beam spot 135 on biosensor 102 can cause a wavelength shift large enough to be mistaken for biological activity. Optical readers thus need to account for this non-homogeneity in order for the measurements to be repeatable. It is therefore desirable that microplate positioning within the optical reader be as accurate as possible. This requires both position detection capability and positioning capability, which are discussed in greater detail below.

Single-Channel Scanning Optical Reader System

Figure 5:
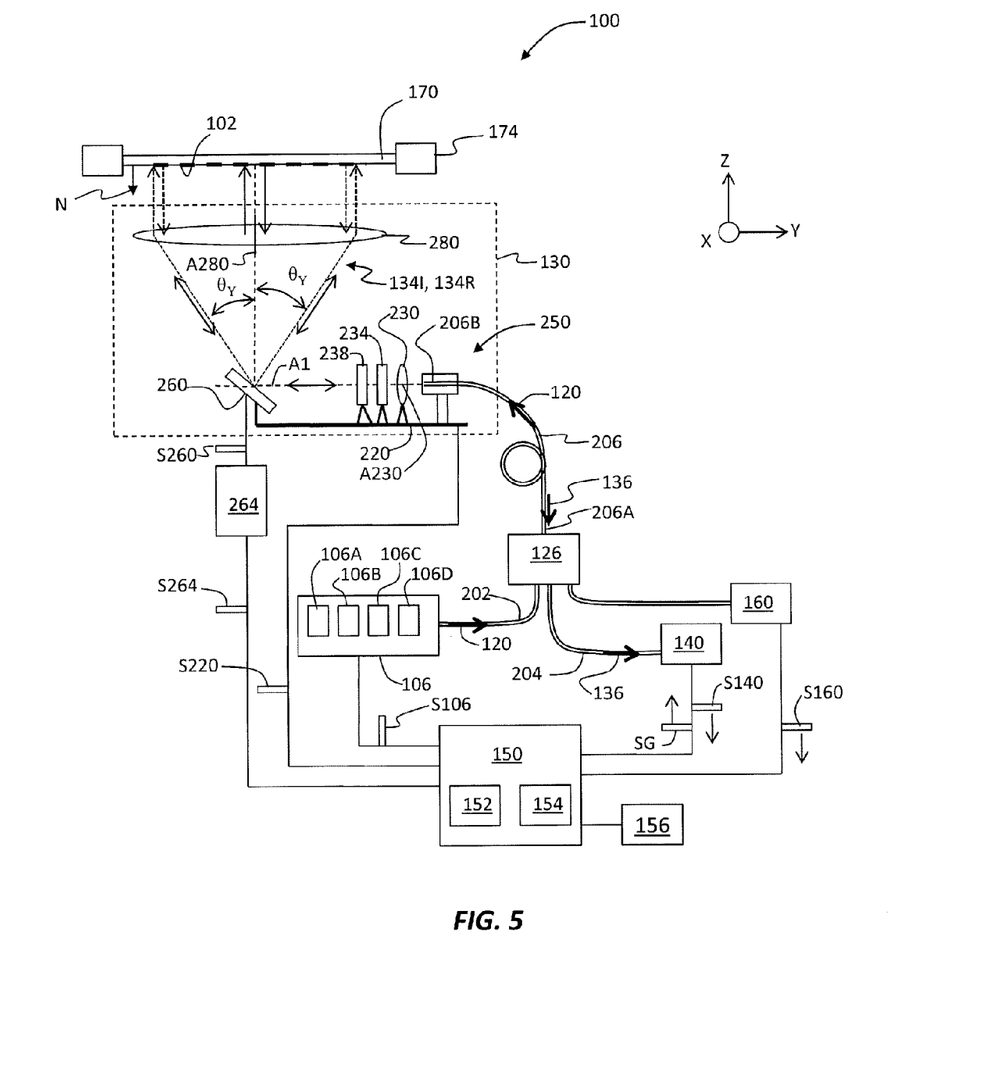
FIG. 5 is a detailed schematic diagram of a single-channel embodiment of a scanning optical reader system of the disclosure.

FIG. 5 is a detailed schematic diagram of an example single-channel embodiment of system 100. Cartesian X-Y-Z coordinates are shown for reference. An exemplary light source assembly 106 comprises a light source 106A, a variable optical attenuator 106B, a polarization scrambler 106C and an optical isolator 106D. Polarization scrambler 106C serves to randomize the polarization of light 120, and optical isolator 106D serves to prevent scattered or reflected light from returning to light source 106A.

An exemplary light source 106A includes a wide spectrum source such as a superluminous diode (SLD). Light source assembly 106 is optically connected by a first optical fiber section 202 to coupling device 126, which in the present embodiment is a 1×2 fiber splitter. Spectrometer unit 140 comprises a spectrometer, such as an HR-2000 spectrometer, available from Ocean Optics, Dunedin, Fla. Spectrometer unit 140 can be connected by a second optical fiber section 204 to coupling device 126. A third optical fiber section 206 can be connected at one end 206A to coupling device 126, while the other end portion 206B can be mounted on an X-Y-Z translation stage 220.

Also mounted on translation stage 220 can be a focusing lens 230 having a focal length f2, a linear polarizer 234 and a quarter-wave plate 238. Note that focusing lens 230 may comprise one or more optical elements. Fiber section end 206A, focusing lens 230, linear polarizer 234 and quarter-wave plate 238 constitute an adjustable beam-forming optical system 250 that shares the aforementioned optical axis A1.

In embodiments, translation using translation state 220 can be accomplished manually, while in other embodiments can be accomplished automatically under the control of controller 150 via a control signal 5220. In an exemplary embodiment, the first, second, and third fiber sections 202, 204 and 206 can be single-mode (SM) fiber sections.

Figure 6:
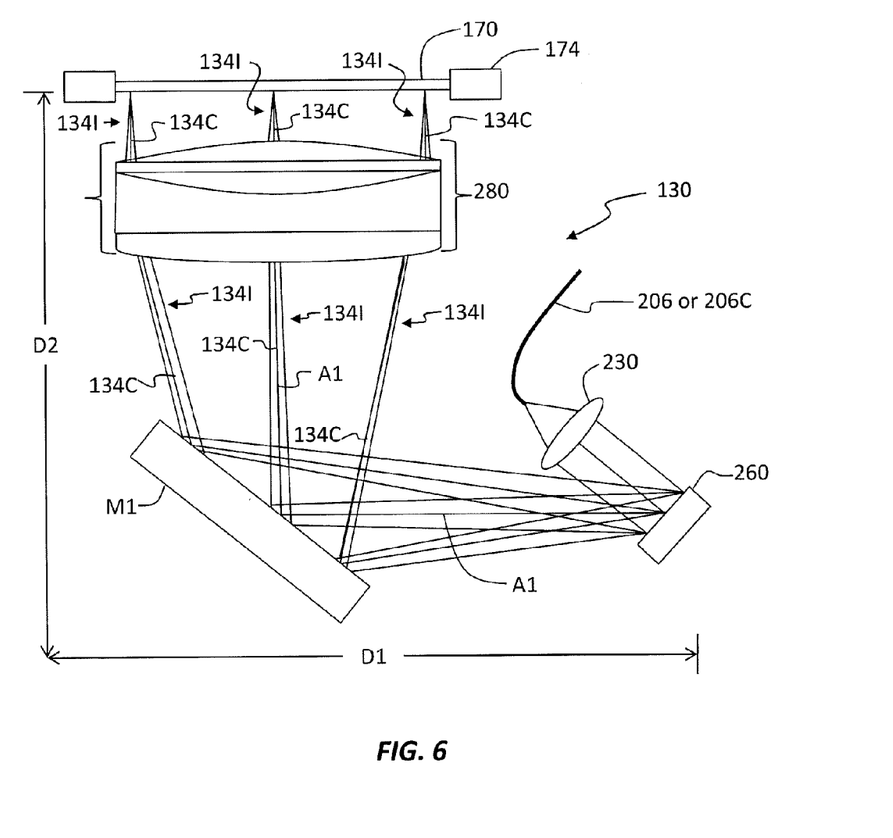
FIG. 6 is a close-up schematic diagram of an exemplary scanning optical system that includes a scanning mirror device, a fold mirror, and an f-theta focusing lens.

System 100 includes a scanning mirror device 260 arranged along optical axis A1 adjacent beam-forming optical system 250. FIG. 6 is a close-up schematic diagram of an exemplary scanning optical system 130 that includes beam-forming optical system 250 and scanning mirror device 260. Scanning mirror device 260 can be, for example, a micro-electro-mechanical system—(MEMS)—based mirror, such as is available from Mirrorcle Technologies, Inc., Albany, Calif., or from Texas Instruments, Dallas, Tex., as model TALP 1011, for example. Other exemplary embodiments of scanning mirror device 260 can include a scanning galvanometer, a flexure-based scanning mirror, an oscillating plane mirror, a rotating multifaceted mirror, and a piezo-electric-driven mirror.

Scanning mirror device 260 can be adapted to scan in at least one dimension (1D) and preferably two-dimensions (2D) (i.e., along axes X and Y, thereby defining associated scanning angles $\theta_X$ and $\theta_Y$). Scanning mirror device 260 can be operably connected to a mirror device driver 264, which may be based on voltage or current depending on the nature of scanning mirror device 260. In embodiments, scanning mirror device 260 can be mounted on translation stage 220. In an example, mirror device driver 264 comprises a multi-axis motion controller, as introduced and discussed below.

A field lens 280 can be arranged along optical axis A1 adjacent scanning mirror device 260 and opposite beam-forming optical system 250. In embodiments, field lens 280 has an F-theta configuration wherein light from any angle $\theta$ is directed substantially parallel to optical axis A1 (i.e., $\beta \sim 0°$). Suitable F-theta field lenses 280 are commercially available from optics suppliers, such as Edmund Optics, Barrington, N.J. Field lens 280 has a focal length f1 and comprises at least one optical element. In embodiments, field lens 280 comprises multiple optical elements, including at least one mirror, or at least one lens, or a combination of at least one mirror and at least one lens. In an exemplary embodiment, field lens 280 includes one or more aspherical surfaces.

System 100 also includes the aforementioned microplate holder 174 configured to operably support microplate 170, which in turn is configured to operably support an array of biosensors 102. In an exemplary embodiment, the position of microplate holder 174 is adjustable so that the position of microplate 170 can be adjusted relative to optical axis A1. Scanning mirror device 260 is located at the focus of field lens 280, i.e., at a distance f1 from the field lens.

System 100 of FIG. 5 is also configured in an example with aforementioned photodetector 160 optically connected to circulator 126.

System 100 of FIG. 6 illustrates an exemplary scanning optical system 130 shown optically coupled to beam-forming optical system 250 and that includes scanning mirror device 260, a fold mirror M1, and f-theta field lens 280. Also shown is microplate holder 174 with microplate 170 supported thereby. Fold mirror M1 can be used to fold optical axis A1 and thus fold the optical path to make scanning optical system 130 more compact. In embodiments, focusing lens 230 has a focal length f2=10 mm and field lens 280 has a focal length f1=200 mm with an aperture of 72 mm. This particular configuration for scanning optical system 130 fits within dimensions L1×L2=140 mm×140 mm and thus has a relatively compact form factor. In embodiments, beam-forming optical system 250 can be included in scanning optical system 130.

The size of the microplate 170 that can be scanned by scanning mirror device 260 is given by the tangent of the mirror deflection multiplied by the focal length of the field lens 280. So, with +/−10 degrees of optical deflection and a 200 mm focal length field lens 280, a 72 mm area can be scanned in both the X- and Y-directions.

An exemplary scanning optical system 130 of FIG. 6 is capable of interrogating a single microplate column of biosensors 102 when configured in a standard microplate format of sixteen wells per column on a 4.5 mm pitch, or about a 72 mm total distance. An exemplary nominal size of beam spot 135 formed by incident optical beam 134I at microplate 170 is 0.1 mm at $1/e^2$ (diameter) and an exemplary beam diameter of the incident optical beam at scanning mirror device 260 is 2 mm at $1/e^2$. FIG. 6 illustrates incident optical beam 134I at three different scan positions (angles). The central ray of incident optical beam 134I is denoted 134C. Note the incident optical beam 134I is a converging beam at microplate 170, with the central rays 134C being parallel to optical axis A1 at the microplate.

As discussed above, exemplary scanning mirror device 260 is a MEMS-based mirror (such as the aforementioned TALP1011 from Texas Instruments), which in an example has a clear aperture of 3.2 mm×3.6 mm and optical scanning angles $\theta_X$ and $\theta_Y$ of +/−10°. The variation of incidence angle $\beta$ of incident optical beam 134R over microplate 170 due to aberrations in an exemplary field lens 280 was found in one example system 100 to be less than 0.3 mRd.

Controller 150 is operably connected to light source assembly 106, spectrometer unit 140 and mirror device driver 264, and is configured (e.g., via software embodied in a computer readable medium such as in processor 152 or memory 154) to control the operation of system 100 as described below. In embodiments, controller 150 can be configured with a General Purpose Interface Bus (GPIB) and the devices to which the controller is operably connected can be configured to communicate with the controller using the GPIB.

With reference again to FIG. 5, in the general operation of system 100, controller 150 sends a light source control signal S106 to light source assembly 106 to cause the light source assembly to generate light 120, which is coupled into first fiber section 202 as guided light. Light 120 travels down first fiber section 202 and to third fiber section 206 via coupling device 126. Light 120 is then processed by beam-forming optical system 250, which forms incident optical beam 134I. Incident optical beam 134I is then selectively deflected by scanning mirror device 260 under the operation of a control signal S260 from mirror device driver 264, which in turn is activated by a control signal S264 from controller 150.

Because scanning mirror device 260 is located at the focus of field lens 280, in the region between the field lens and microplate, the incident optical beam 134I (or, more precisely, the central ray 134C of this beam) is parallel to optical axis A1 for all deflection angles. System 100 can be adjusted so that incident optical beam 134I remains substantially normal to microplate 170 as the beam scans the microplate.

Incident optical beam 134I scans over biosensor 104 as described below and reflects therefrom at substantially normal incidence to form reflected optical beam 134R. Reflected optical beam 134R thus travels substantially the reverse optical path of incident optical beam 134I and is coupled back via beam-forming optical system 250 into third fiber section 206 at end portion 206B and becomes guided light signal 136. Guided light signal 136 then travels through third optical fiber section 206 to second optical fiber section 204 via coupling device 126, where it is received and spectrally decomposed by spectrometer unit 140. Spectrometer unit 140 provides electrical signal S140 representative of the spectral information in reflected optical beam 134R to controller 150 and to memory 154 therein. Memory 154 stores the spectral information as a function of the scanning angles ($\theta_X$, $\theta_Y$). In embodiments, memory 154 stores and processor 152 runs analysis software for analyzing and visualizing the spectral information, such as Matlab, available from Mathworks, Inc., Natick, Mass.

In embodiments, memory 154 stores a number (e.g., 50) of spectra for each biosensor 102, and processor 152 sums the spectra to obtain a total spectra, and then calculates the centroid to determine resonant wavelength $\lambda_R$. In embodiments, tens, hundreds, or thousands of spectra can be saved in memory 154 for processing by processor 152. Spectra measurements can be divided up by, for example, individual biosensors 102 or by columns or rows of biosensors. In another embodiment, the centroid of each spectrum is determined and then the centroids averaged to determine the resonant wavelength $\lambda_R$.

Biosensor Scanning

One method of scanning using system 100 is to operate scanning mirror device 260 to scan one or more biosensors 102 in a single scanning direction. However, a shortcoming of this approach is that the resonance wavelength $\lambda_R$ varies significantly as a function of the position of beam spot 135 across biosensor 102. Accordingly, in this approach the position of beam spot 135 needs to be monitored closely to avoid introducing measurement bias. Examples of biosensor scanning are disclosed in International Publication Number WO2011/017147, which is incorporated by reference herein.

Figure 7:
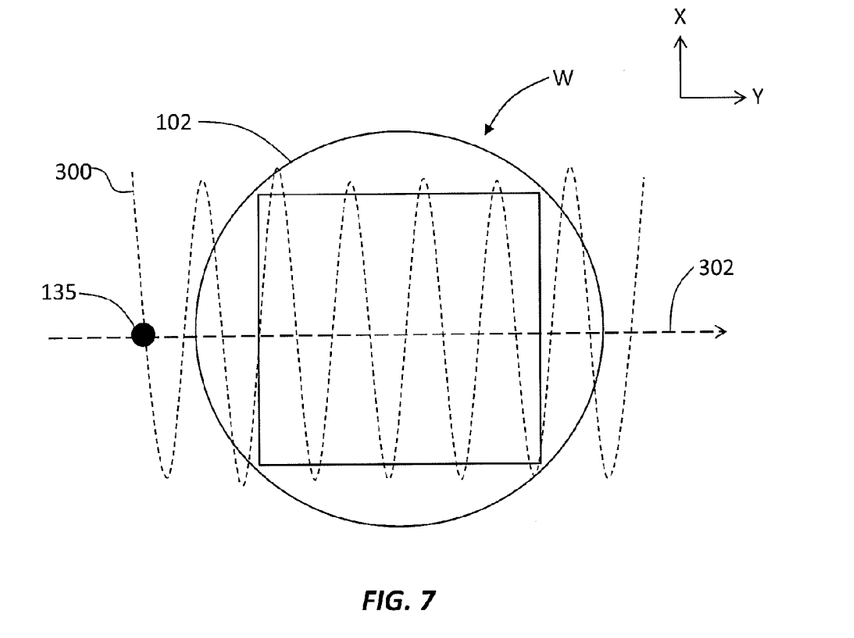
FIG. 7 is a close-up, front-on schematic view of a biosensor showing an example oscillatory scan path (short-dash line) along with its base-line linear component (long-dash line) in the Y-direction.

A preferred method of operating system 100 involves scanning biosensors 102 with incident optical beam 134I in two dimensions X and Y to obtain an integrated measurement of each scanned biosensor. An example of a two-dimensional scan path 300 used to scan biosensor 102 is shown in FIG. 7. Because a MEMS-based mirror scanning device can be driven at a relative high frequency (e.g., ≥100 Hz), it is possible to rapidly perform such a two dimensional scan of a biosensor. In the example scan path 300 of FIG. 7, biosensor 102 is scanned by moving optical beam 134I (and thus beam spot 135) faster in one of the two dimensions to obtain a zig-zag or oscillatory scan path 300 represented as a short-dashed line. The large-dashed line 302 represents the base-line linear motion (i.e., base-line path) in the Y-direction.

In embodiments, system 100 can be configured so that the position of field lens 280 is adjustable relative to scanning mirror device 260 and beam-forming optical system 250. In embodiments, the relative positions of field lens axis A280, scanning mirror device 260 and focusing lens axis A230 are adjustable, i.e., one or more of these elements is displaceable relative to optical axis A1. In embodiments, this adjustability is provided by translation stage 220. The angle of incidence β of incident optical beam 134I relative to microplate 170 is defined by the vector joining the center of the incident optical beam at focusing lens 230 and the apex of field lens 280.

Thus, in embodiments, incidence angle β of incident optical beam 134I can be adjusted by adjusting the relative position of lenses 230 and 280. Such adjustment can be made in embodiments by adjusting translation stage 220 that includes scanning mirror device 260 and focusing lens 230. This operation does not require translation stage 220 to have high precision. By way of example, for a field lens 280 having a focal length f1=200 mm, the alignment precision only needs to be in the order of 0.2 mm to insure that the precision of incidence angle β is within 1 mrad. This adjustability makes system 100 substantially insensitive to microplate misalignment.

Defining the Scan Path

Scanning mirror device 260 of scanning optical system 130 has limits on how fast it can respond to control signals 5260 from mirror device driver 264 and is subject to vibration due to mechanical resonance. When scanning mirror device 260 is driven to guide beam spot 135 over certain types of scan paths 300 that include rapid changes in the oscillatory motion relative to a center position or baseline motion. The rapid changes in the oscillatory motion can include transitioning to and from no oscillatory motion, vibrations and ringing that can reach the point that they significantly degrade the performance of optical reader system 100.

Figure 8:
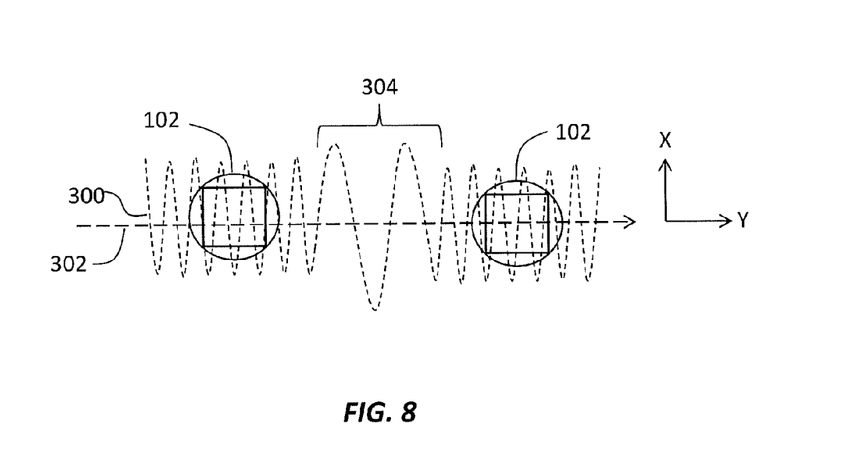
FIG. 8 is a schematic front-on view of two biosensors showing an example scan path that includes a transition section between adjacent biosensors.

FIG. 8 is a schematic front-on view of two biosensors 102 showing an example scan path 300 that includes a transition section 304 between the two biosensors where the frequency of the oscillatory motion changes so that light spot appears to move more quickly between the biosensors. In examples, the frequency of the oscillation (in time) of scan path 300 is not changed but the speed of base-line path 302 is increased and the phase of oscillation is changed, so the oscillation looks like it slows down. Example changes in scan path 300 include providing fast jumps in the center of oscillation, providing fast jumps in the magnitude of the oscillation, including changing from X-oscillation to Y-oscillation (which can be considered a simultaneous change of x from something to nothing, and change in y from nothing to something), and changing the oscillation phase.

Figure 9:
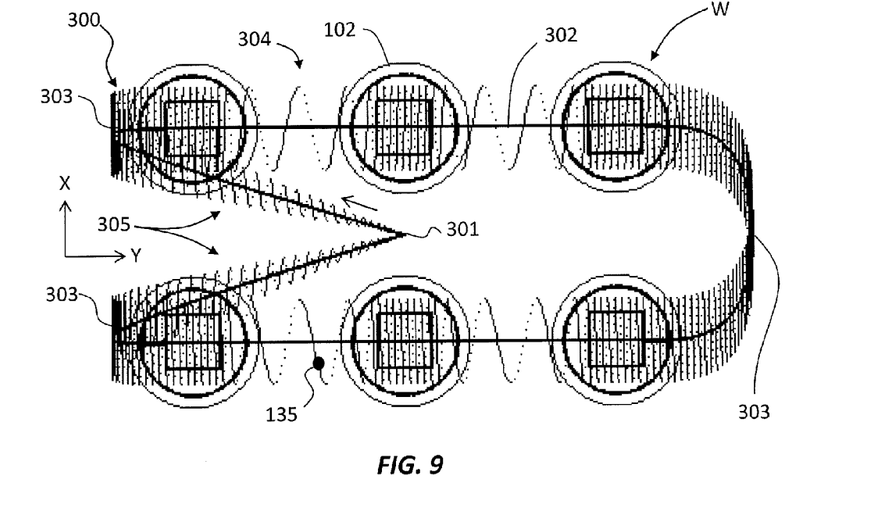
FIG. 9 is a schematic front-on view of six biosensors illustrating an example scan path for scanning the six biosensors.
Figure 10:
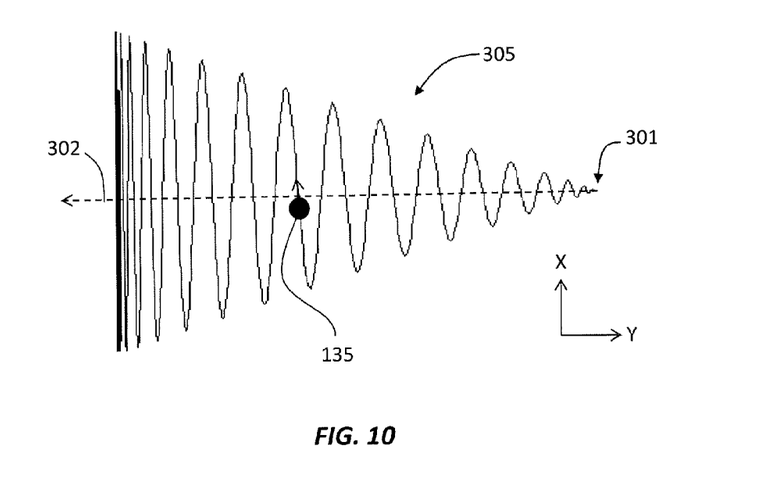
FIG. 10 is a close-up plot of a ramp-up section of the scan path of FIG. 9.

FIG. 9 is a schematic front-on view of six biosensors 102 illustrating an example scan path 300 for scanning the six biosensors. The scan path 300 includes a starting/ending point 301, ramp-up and ramp-down sections 305, base-line path 302, turning points 303 and transition sections 304. FIG. 10 is a close-up plot of ramp-up section 305 of the scan path 300 of FIG. 9. In the scan path 300 of FIG. 9, in one embodiment, the oscillation frequency remains the same and the speed of base-line path 302 is increased or decreased as needed.

Changes in the parameters defining the oscillatory component of scan path 300 can cause unwanted resonant vibration. In certain cases, a discontinuous change in the oscillatory component of scan path 300 may lead to vibration as or more severe than a similar change in the baseline path 302. When a force is modulated at a certain frequency, its frequency spectrum can shift by that frequency. This can result in the excitation of a resonance that can cause unwanted vibrations. It is noted that discontinuous changes often occur because the equation of motion that defines scan path 300 includes "constants" such frequency, phase and amplitudes that are not really constants but need to be changed periodically. These kinds of abrupt changes to the "constants" can give rise to the aforementioned unwanted vibrations. It is therefore desirable to define scan path 300 in a manner that reduces or minimizes discontinuities in the scan path, as well as in the scan path derivatives (e.g., velocity and acceleration).

Scan path 300 can have a number of desirable properties, such as phase matching, coordinated motion and ease of specification. Phase matching ensures that parameters scan paths 300 having baseline and oscillatory motions with the same amplitude, direction, frequency and phase produce exactly the same motion of beam spot 135. Two otherwise identical scan paths can be out of phase unless the time separating the scan paths is exactly one period of the oscillation. It is desirable to have a mechanism for changing the phase of two such scan paths 300 to compensate for any phase difference in their time separation.

It is also desirable that the baseline and oscillation motion parameters can change over the same period of time. An example where this property is desirable is for an initial ramp-up section 305 of scan path 300 where the amplitude of the oscillatory motion increases from zero to a required value over same time the baseline motion is reaching its assigned position and velocity for scanning the first biosensor (e.g., top-left well W; see e.g., FIG. 2; see also FIGS. 9 and 10).

It is also desirable to be able to specify the oscillatory and baseline motions with relative ease to optimize or otherwise increase the efficiency of the biosensor reading process. This might include, for example, specifying the initial and final position and velocity of the baseline position and of each oscillation parameter over some specified time.

An aspect of the disclosure includes defining a scan path 300 that judiciously combines oscillatory motion with non-oscillating baseline motion by defining more axes than just the two main axes of motion, i.e., more than just the X and Y axes. A scan path 300 defined in this manner enables the reduction of resonant vibration (observed as ringing in the motion) in the scanning optical system 130 and scanning mirror device 260 therein. In an example, this is accomplished by taking commanded position outputs of a multi-axis (e.g., six-axis) motion controller and performing additional processing to control the Cartesian movement of the optical scanning system, together with the amplitude, direction, frequency and phase of a superimposed oscillation.

Figure 11:
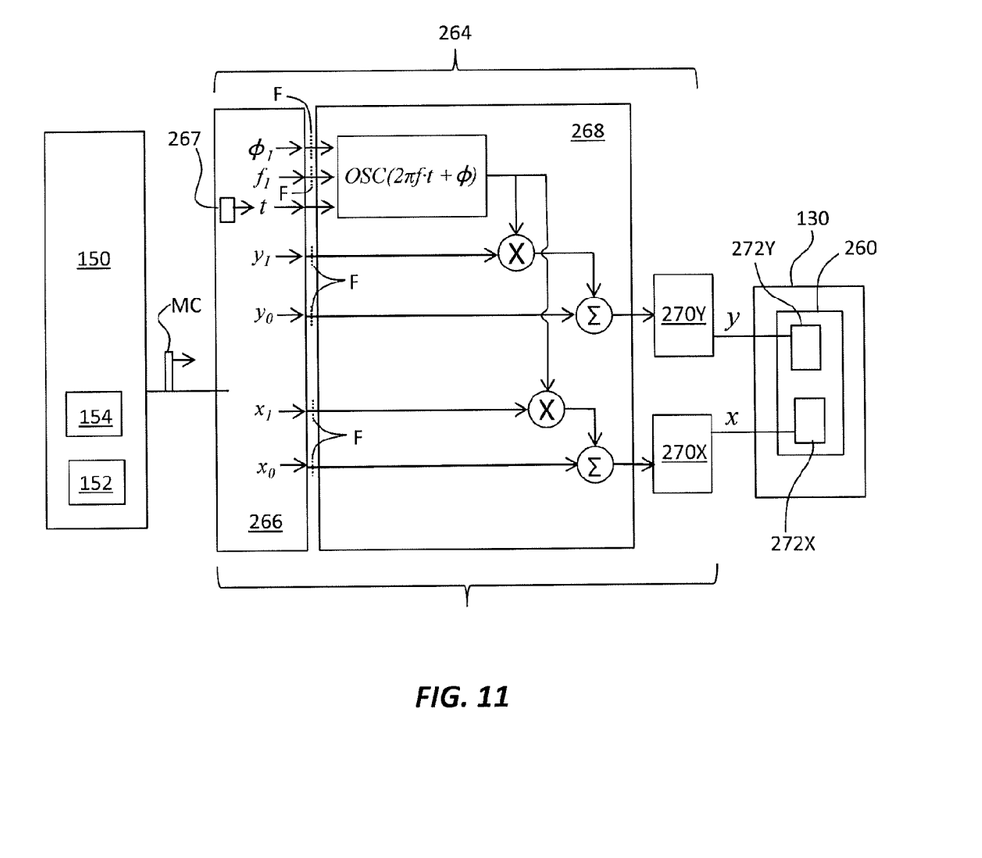
FIG. 11 is a schematic diagram of a portion of an optical reader system illustrating an example mirror device driver operably connected to a scanning mirror device of a scanning optical system.

FIG. 11 is a schematic diagram of a portion of system 10 illustrating an example mirror device driver 264 operably connected to scanning mirror device 260 of scanning optical system 130. Mirror device driver 264 includes a multi-axis (e.g., six-axis) motion controller 266 operably connected to an input end of a post-processor 268, and two digital amplifiers 270 operably connected to an output end of the post-processor. The digital amplifiers 270 are configured to convert the digital input into an amplified drive output capable of powering actuators 272. Examples of drive outputs include analog current and pulse-width modulated (PWM) current. Thus, in an example, digital amplifiers 270X and 270Y are respectively configured to receive digital x and y inputs and provide analog or PWM x and y outputs. In FIG. 11 and in FIG. 13, the symbol X in a circle stands for a multiplication operation and the symbol Σ in a circle stands for a summation operation.

An example multi-axis motion controller 266 may be, for example, a PMAC2 Turbo six-axis motion controller available from Delta Tau Data Systems, Inc. of Chatsworth, Calif., or like multi-axis controller. In an example, multi-axis controller 266 is configured to control digital amplifiers 270 via a digital interface such as a stepper motor amplifier, a "Step and Direction" interface, or the SERCOS (Serial Real-time Communication System) communication protocol over optical fibers. Motion controller 266 includes a clock 267 that generates a clock signal represented by time t in FIG. 11. In examples, the synchronization of the various signals provides the system timing, while in other examples, the clock signal represented by time t provides the system timing.

In an example embodiment, digital amplifiers 270X and 270Y are respectively coupled to electromagnets 272X and 272Y of scanning mirror device 260, which electromagnets are respectively configured to control the X and Y orientations of the scanning mirror device in response to respective drive currents from the digital amplifiers. In example, digital amplifiers 270X and 270Y can be used to close the feedback loop, as opposed to being closed at controller 150. An open-loop configuration may also be employed.

With continuing reference to FIG. 11, in operation, a user of system 100 specifies move commands MC that include basic information about a particular scan path 300. Example move commands MC include starting and ending positions of the desired scan path 300, information about the velocity (e.g., at least one velocity limit) of the scan spot 135 at different locations along the scan path, information about the acceleration (e.g., at least one acceleration limit), an amount of time to move the scan spot between different positions along the scan path, (e.g., from the starting to ending positions), etc. A commercial general purpose multi-axis motion controller 266 typically has a wide range of ways a user can specify move commands MC, from constant-speed scanning to as-fast-as-possible point-to-point moves. In an example, the move commands MC are provided to the six-axis motion controller 266 by controller 150 as a signal MC, as shown in FIG. 11.

In an example, the move commands MC include a command that defines an amount of time to carry out the move, i.e., to move light spot 135 over at least a portion of scan path 300, and further includes for each axis: a start value, an end value, a velocity limit, an acceleration limit, a start velocity, and an end velocity. Thus, in an example, the move commands MC for x and y axes are selected from the group of move commands comprising: an x start position, a y start position, an x end position, a y end position, a velocity limit, an acceleration limit, an x start velocity, a y start velocity, an x end velocity, a y end velocity, and an amount of time from the x and y start positions to the x and y end positions. Analogous move commands MC can be generates for the other four axes.

Multi-axis motion controller 266 receives and processes the move commands MC. Multi-axis motion controller 266 includes motion-planning algorithms and actuator algorithms that are standard and that are usually proprietary to the controller manufacturer. Such motion-planning algorithms and actuator algorithms need not be known for the purposes of carrying out the various aspects of this disclosure relating to defining different scan paths 300. The motion-planning algorithms and actuator algorithms produce actuator functions for each of the multiple axes. The actuator function for each output axis can be a function of time. Typically it is a list of functions, each valid for a specific duration and that meet the user move commands MC. The actuator functions describe axis positions at any given time. The motion controller continuously updates time and substitutes time into each actuator function. The commanded positions x and y are numbers (values) for the different axes that specifies a value for that axis at the specified time t. Commanded positions are used as set points for axis control.

In an example, the six axes include: an x-baseline coordinate $x_0$, a y-baseline coordinate $y_0$, an x-direction oscillation amplitude $x_1$, a y-direction oscillation amplitude $y_1$, an oscillation frequency f and a phase $\phi$. The move commands MC relating to these axes are thus processed by multi-axis motion controller 266 to create commanded positions for each of these axes. The time reference t generated in multi-axis motion controller 266 by clock 267 can be separately provided as well.

Rather than the commanded positions being sent directly to digital amplifiers and then onto scanning optical system 130, in an example they are sent to a post-processor 268. Post-processor 268 is configured to perform calculations, based on the inputted command positions, that define parameterized command positions (x(t), y(t)) that in turn define x and y motion associated with scan path 300, namely:

$$x = x_0 + x_1 \cdot \text{OSC}(2\pi \cdot f \cdot t + \phi) \quad \text{(Eq. 1a)}$$

$$y = y_0 + y_1 \cdot \text{OSC}(2\pi \cdot f \cdot t + \phi) \quad \text{(Eq. 1b)}$$

where OSC stands for an oscillatory function.

Generally, oscillatory function OSC is a function that periodically varies between an upper and a lower limit. Examples of oscillatory function OSC include at least one of: a sine function, a cosine function, a square wave, a triangular wave, a periodic wave made up of polynomial segments, a periodic wave made up of hyperbolic segments, a sigmoid function, and a periodic function filtered to remove select resonant frequencies of the scanning optical system. Combinations of these oscillatory functions can also be employed.

Thus, in an example where oscillatory function OSC is the sin function, Eqs. 1a and 1b become:

$$x = x_0 + x_1 \cdot \sin(2\pi \cdot f \cdot t + \phi) \quad \text{(Eq. 2a)}$$

$$y = y_0 + y_1 \cdot \sin(2\pi \cdot f \cdot t + \phi) \quad \text{(Eq. 2b)}$$

In another example, oscillatory function OSC can be defined piecewise, such as in the following example, where $\psi = 2\pi \cdot f \cdot t + \phi$.

$$OSC(\psi) \equiv \begin{vmatrix} \frac{1}{2}(\cos(2\psi) + 1) & 0 \leq \pi < \frac{\pi}{2} \\ -\frac{1}{2}(\cos(2\psi) + 1) & \frac{\pi}{2} \leq x < \frac{3\pi}{2} \\ \frac{1}{2}(\cos(2\psi) + 1) & \frac{3\pi}{2} \leq x < 2\pi \\ p(\psi - 2\pi \cdot n) & 2\pi \cdot n \leq x < 2\pi \cdot (n+1), n \neq 0 \end{vmatrix}$$

Figure 12:
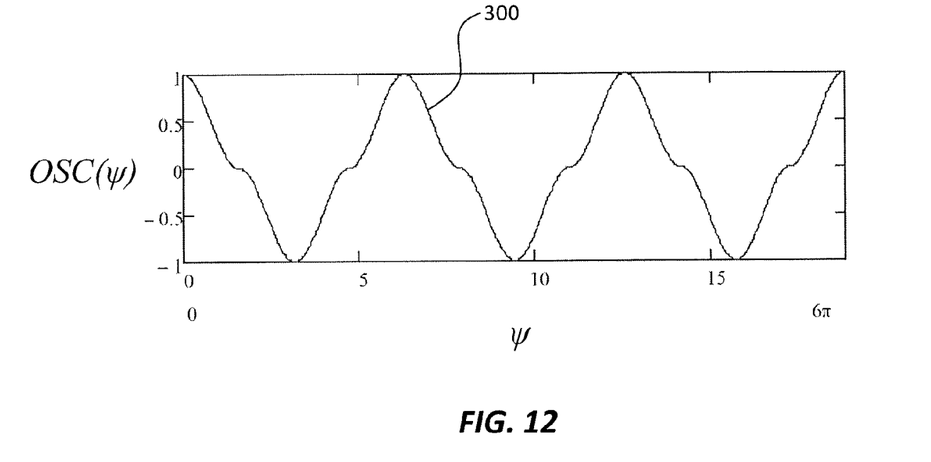
FIG. 12 plots an example oscillatory function OSC.

FIG. 12 plots $OSC(\psi)$ vs. $\psi$. This particular oscillatory function OSC has some interesting properties for scan path 300, including that it stays on biosensor 102 longer and hence collects more data that a pure sinusoid oscillatory function.

Digital amplifiers 270X and 270Y receive the parameterized command positions (x,y) from post-processor 268, amplify the received output and form therefrom a drive output, such as x and y analog currents or x and y PWM currents. The x and y drive outputs are then provided to respective electromagnets 272X and 272Y to drive the scanning mirror device (e.g., a MEMS mirror) to deflect incident optical beam 134I to scan beam spot 135 over the defined scan path 300.

Figure 13:
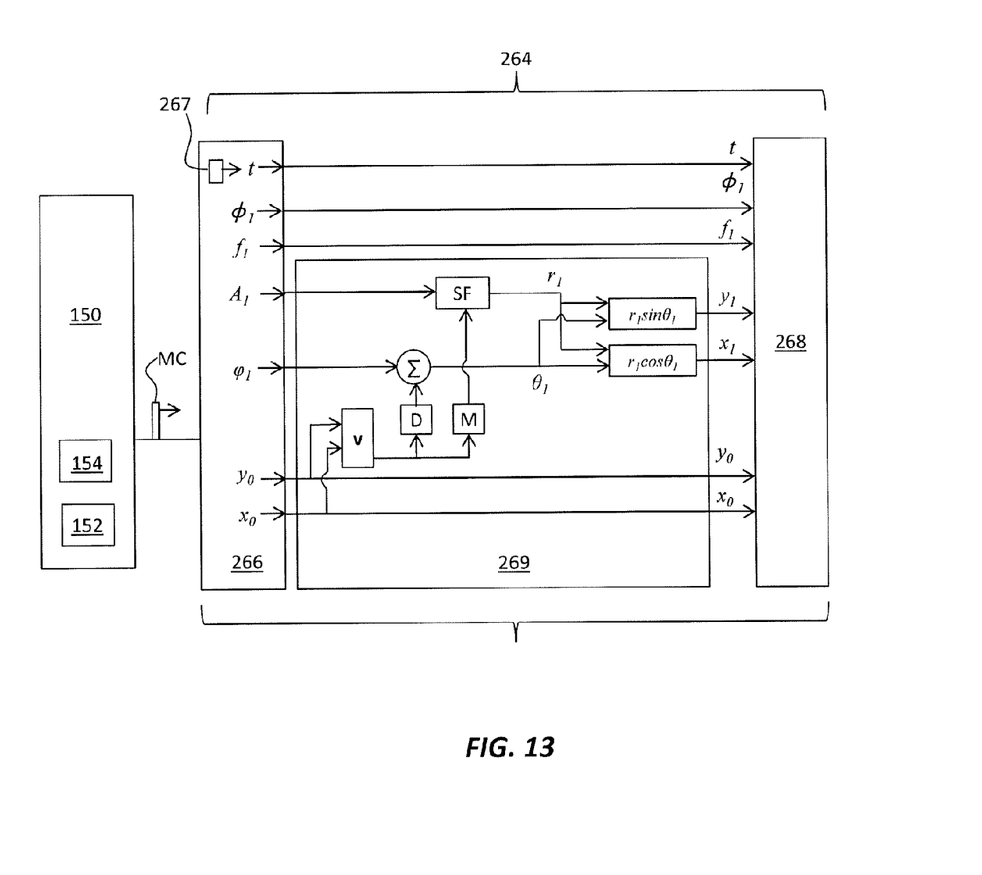
FIG. 13 is similar to FIG. 11 and illustrates an example configuration that includes an intermediate processor between the multi-axis motion controller and the post-processor.

FIG. 13 is similar to FIG. 11 and illustrates an example configuration for mirror-device driver 264 that includes an intermediate processor 269 between multi-axis motion controller 266 and post-processor 268. Intermediate processor 269 is configured to generate oscillation amplitudes ($x_1$, $y_1$) for use by post-processor 268 when the supplied oscillation amplitude $A_1$ is in a direction normal to a baseline direction of travel (motion) $\phi_1$.

It is also possible to define scan path 300 in terms of polar coordinates where oscillation amplitude in the rectangular directions ($x_1$, $y_1$) is defined using radius and angle ($r_1$, $\theta_1$). In the case where the multi-axis motion controller 266 requires Cartesian inputs, an intermediate processing step can be added to perform the conversion from polar-coordinate inputs to Cartesian-coordinate outputs. Thus, the user of system 100 specifies the oscillation amplitude in radius and angle commands (e.g., via controller 150) and the multi-axis controller 266 outputs as radius and angle values ($r_1$, $\theta_1$). The intermediate processor 269 then converts ($r_1$, $\theta_1$) to ($x_1$, $y_1$) using the standard rectangular-to-polar coordinate transformation:

$$x_1 = r_1 \cdot \cos(\theta_1) \quad \text{(Eq. 3a)}$$

$$y_1 = r_1 \cdot \sin(\theta_1) \quad \text{(Eq. 3b)}$$

With reference to scan path 300 of FIG. 9, the move commands MC associated with the beginning portion of the scan path from start/end point 301 to turning point 303 may take the following form (using plain English): Take 0.25 seconds to move from the center of the plate (y, x)=(0,0) to the location (−20,−9), which is immediately left of the first grating. During this same time, increase the sinusoidal amplitude $A_1$ from 0 to 7 mm peak-to-peak. End the y-velocity at 120 mm/s and make all other start and end velocities zero.

At the start of the move command, light spot 135 is stationary at the center of the plate, i.e., at start/end point 301. At the end of the command, light spot 135 is in the position just outside the first RWG biosensor 102, and is moving at 120 mm/s towards this RWG biosensor. The next command moves light spot 135 from the position on one side of the RWG biosensor 102 to a position at the other side of the RWG biosensor at a constant y-velocity of 120 mm/s, while maintaining the same oscillation amplitude, frequency and phase. The rest of scan path 300 of FIG. 9 is described in a similar manner to complete the scan path (i.e., return light spot 135 to start/stop point 301).

Nearly all multi-axis controllers have a velocity control mode as one of their primary modes of operation. However, if there is no velocity control mode on a particular multi-axis controller 266, then intermediate processor 269 can be used to calculate the velocity v of the baseline motion $\phi_1$ by taking the difference between the last two positions and dividing by the time interval it took to travel between the last two positions. This is carried out in intermediate processor 269 in the box labeled v. The other boxes in intermediate processor 269 include a direction box D and a magnitude box M that respectively represent the direction and magnitude ($\|v\|$) of velocity vector v.

If the velocity v of the baseline motion approaches zero, the direction of scan path 300 becomes undefined, so this situation needs to be addressed in intermediate processor 269. This is accomplished through the use of a sigmoid function SF in the box labeled SF in FIG. 13. The sigmoid function SF does nothing if the velocity v is sufficiently large. That is, it allows the input (in this case, the desired oscillation amplitude $A_1$) to pass through unchanged. However, if the velocity is small (i.e., reaches a threshold velocity such as 0.001 mm/s), the sigmoid function SF overrides the oscillation amplitude A1 and sets it to zero, effectively turning off the oscillation. This must be done in a smooth manner. An example sigmoid function SF is given by Eq. 5 below, where $\|v\|$ is the magnitude of the velocity.

$$SF = \frac{2}{1 - \exp(-k\|v\|^2)} \quad \text{(Eq. 5)}$$

If the oscillation amplitude $A_1$ is reduced to zero, held at zero for a short time, and then increased to some required value, both frequency f and phase $\phi$ can be changed in any manner to any value while the amplitude is zero without causing vibration. Only the amplitude itself needs to be considered. This eliminates two potential axes (frequency and phase) for the trade of some cycle time. In an example of the operation of system 100, scanning mirror device 260 may be placed in a substantially unpowered state when idle (e.g., for reliability reasons). This allows the oscillation amplitude $A_1$ to be zero at the start of a measurement cycle. The phase $\phi$ can be set to zero at this point.

In the above examples, at least one of the phase $\phi$ and frequency f may be fixed, i.e., not vary as a function of time. Alternatively, the phase $\phi$ or frequency f may be changed in a discontinuous manner at any point where the amplitude of the oscillation is ramped down to zero in a smooth manner. It can then be ramped back up again.

As discussed above, the oscillation need not be purely a sinusoidal but can be some other form of oscillation. Further, two or more oscillatory functions may be combined (e.g., superimposed). For example, two sinusoids can be combined, each at different fixed frequency and phase. To change between frequencies, one sinusoid is ramped up while the other is ramped down. The superposition of oscillation may be performed digitally or using analog circuits. The oscillation itself can be generated using analog circuits, as described in U.S. Pat. No. 7,869,910.

The oscillating component of scan path 300 in many cases will be relatively rapid as compared to the baseline motion $\phi_1$.

Therefore, axis values can be calculated less often than calculating the value of the oscillation waveform without a noticeable degradation of performance. This saves memory space and reduces calculation time, which in turn reduces the amount of calculation power needed.

For example, suppose a 50 Hz sine wave sampled at 2000 Hz (40 points per period) gives sufficient quality for the particular biosensor measurement application. Axis parameters include the baseline motion $\phi_1$ plus oscillation amplitude $A_1$, frequency f and phase $\phi$, etc., might only need to updated at 200 Hz for acceptable quality. This means the axis values might be calculated only once in ten update cycles.

In an example embodiment where the frequency f of the scan path oscillation is fixed, the oscillatory function OSC can be defined in a look-up table (e.g., a 120-point look-up table). Axes are updated at a rate four times lower than for the oscillatory function OSC. In fact, only one of the four axes are updated for each recalculation of the scan path output, with each axis being updated in turn. This reduces the processing requirements by a factor of almost four, because the addition, multiplication and selection of the OSC value from a look-up table are relatively insignificant compared with evaluating the scan path for a specific time. The quality of the final result approaches that of a faster processor while resources are not wasted recalculating values that barely changed between sample times.

It is also noted that the phase axis value may be altered so that $\omega \cdot t + \phi$ (where $\omega = 2\pi f$) has a particular angle at a particular time to achieve phase matching. This involves examining $\omega \cdot t + \phi$ phase at the calculated start of a future move, then calculating a path to the desired phase before that future move starts. Such a move is called a "blended move," where it modifies a path "on-the-fly".

In an example, mirror device driver 264 optionally includes filters F (illustrated schematically as dotted lines) configured to reduce resonance effects. Example filters F are low-pass or notch filters that target specific resonance frequencies and are arranged in one example as shown in FIG. 11 at the six outputs of motion controller 266. Other locations for filters F can also be employed, though generally it is better to arrange them upstream of the formation of the sine wave signal so that the sine wave signal is not inadvertently filtered.

It will be apparent to those skilled in the art that various modifications to the preferred embodiment of the disclosure as described herein can be made without departing from the scope of the disclosure as defined in the appended claims. Thus, the disclosure covers the modifications and variations provided they come within the scope of the appended claims and the equivalents thereto.

What is claimed is:

1. A method of defining a scan path using a scanning optical system to scan a beam spot formed by a light beam over one or more biosensors supported by a microplate, comprising:
   inputting to a multi-axis motion controller move commands associated with the scan path as defined by multiple axis comprising an x-baseline coordinate $x_0$, a y-baseline coordinate $y_0$, an x-direction oscillation amplitude $x_1$, a y-direction oscillation amplitude $y_1$, an oscillation frequency f and a phase $\phi$;
   outputting from the multi-axis motion controller commanded positions for each of the multiple axes;
   receiving the commanded positions with a post-processor and generating therein parameterized commanded positions x and y defined the following equations where t is time and OSC is an oscillatory function:

$x = x_0 + x_1 \cdot OSC(2\pi \cdot f \cdot t + \phi)$ and $y = y_0 + y_1 \cdot OSC(2\pi \cdot f \cdot t + \phi)$; and inputting the parameterized commanded positions x and y to a scanning optical system to cause the scanning optical system to deflect the light beam to scan the beam spot over the scan path.

2. The method of claim 1, wherein the oscillatory function OSC includes at least one function selected from the group of functions comprising: a sine function, a cosine function, a square wave, a triangular wave, a periodic wave made up of polynomial segments, a periodic wave made up of hyperbolic segments, a sigmoid function, and a periodic function filtered to remove select resonant frequencies of the scanning optical system.

3. The method of claim 1, wherein the parameterized commanded positions x and y are digital, and further comprising;
   converting the digital parameterized commanded positions x and y to parameterized drive output positions x and y; and
   amplifying the parameterized drive output positions x and y and inputting same into the scanning optical system.

4. The method of claim 3, further comprising generating the amplified commanded positions x and y as respective x and y currents.

5. The method of claim 1, wherein the scanning optical system includes one of a scanning galvanometer, a flexure-based scanning mirror, a micro-electro-mechanical system (MEMS) mirror, an oscillating plane mirror, a rotating multifaceted mirror, and a piezo-electric-driven mirror.

6. The method of claim 1, further comprising:
   defining one of the move command as an amount of time to move the light spot over at least a portion of the scan path; and
   defining the following move commands for each axis: a start value, an end value, a velocity limit, an acceleration limit, a start velocity, and an end velocity.

7. The method of claim 1, further comprising inputting the move commands to the multi-axis motion controller from a system controller.

8. The method of claim 1, wherein the scan path has a velocity and an oscillation amplitude, and further comprising smoothly reducing the oscillation amplitude to zero as the scan path velocity decreases to a threshold value.

9. The method of claim 8, further comprising employing a sigmoid function in smoothly reducing the oscillation amplitude.

10. The method of claim 1, wherein the scan path includes a baseline component, and wherein baseline component includes sections of the scan path between adjacent biosensors that have a greater velocity than baseline component sections of the scan path that scan over the biosensors.

11. A system for defining a scan path for a beam spot formed by a light beam over a microplate that operably supports at least one biosensor, comprising:
   a multi-axis motion controller configured to receive move commands associated with the scan path as defined by respective axes, the axes including an x-baseline coordinate $x_0$, a y-baseline coordinate $y_0$, an x-direction oscillation amplitude $x_1$, a y-direction oscillation amplitude $y_1$, an oscillation frequency f and a phase $\phi$, and output commanded positions for each of the multiple axes;
   a post-processor configured to receive the commanded positions and generate therefrom parameterized commanded positions x and y defined by the following equations where t is time and OSC is an oscillatory function:

$x=x_0+x_1 \cdot OSC(2\pi \cdot f \cdot t+\phi)$ and $y=y_0+y_1 \cdot OSC(2\pi \cdot f \cdot t+\phi)$; and a scanning optical system configured to receive the parameterized commanded positions and in response thereto deflect the light beam to scan the beam spot over the scan path.

12. The system of claim 11, wherein the oscillatory function OSC includes at least one function selected from the group of functions comprising: a sine function, a cosine function, a square wave, a triangular wave, a periodic wave made up of polynomial segments, a periodic wave made up of hyperbolic segments, a sigmoid function, and a periodic function filtered to remove select resonant frequencies of the scanning optical system.

13. The system of claim 11, further comprising first and second digital amplifiers operably connected to the post-processor and respectively configured to convert the digital parameterized commanded positions x and y to parameterized drive output positions x and y and to amplify the parameterized drive output positions x and y.

14. The system of claim 13, further comprising generating the amplified commanded positions x and y as respective x and y currents.

15. The system of claim 11, wherein the scanning optical system includes one of a scanning galvanometer, a flexure-based scanning mirror, a micro-electro-mechanical system (MEMS) mirror, an oscillating plane mirror, a rotating multifaceted mirror, and a piezo-electric-driven mirror.

16. The system of claim 11, further comprising: a system controller operably connected to the multi-axis controller and configured to input the move commands to the multi-axis controller.

17. The system of claim 11, wherein the scan path has a velocity and an oscillation amplitude, and further comprising the post-processor being configured to smoothly reduce the oscillation amplitude to zero as the scan path velocity decreases to a threshold value.

18. The system of claim 17, further comprising the post-processor configured to employ a sigmoid function to smoothly reduce the oscillation amplitude.

19. The system of claim 18, further comprising an intermediate processor operably arranged between the multi-axis motion controller and the post-processor, the intermediate processor configured to express the parameterized commanded positions x and y in polar coordinates.

20. A method of defining a scan path for a beam spot formed by a scanning optical system, comprising:
inputting to a multi-axis motion controller move commands associated with the scan path as defined multiple axes, the multiple axes including an x-baseline coordinate $x_0$, a y-baseline coordinate $y_0$, an x-direction oscillation amplitude $x_1$, a y-direction oscillation amplitude $y_1$, an oscillation frequency f and a phase $\phi$;
outputting from the multi-axis motion controller digital commanded positions for each of the multiple axes;
receiving the digital commanded positions with a post-processor and generating therein analog or pulse-wave modulated parameterized commanded positions x and y that each include a baseline motion component and an oscillating motion component; and
inputting the analog or pulse-wave modulated parameterized commanded positions to a scanning optical system to cause the scanning optical system to deflect a light beam to scan the beam spot over the scan path.

21. The method of claim 20, wherein the analog or pulse-wave modulated parameterized commanded positions x and y are defined by the following equations where t is time:

$x=x_0+x_1 \cdot \sin(2\pi \cdot f \cdot t+\phi)$ and $y=y_0+y_1 \cdot \sin(2\pi \cdot f \cdot t+\phi)$.

* * * * *